US010973485B1

(12) United States Patent
Douglas et al.

(10) Patent No.: US 10,973,485 B1
(45) Date of Patent: Apr. 13, 2021

(54) ENHANCED VOLUME VIEWING

(71) Applicants: David Byron Douglas, Winter Park, FL (US); Robert Edwin Douglas, Winter Park, FL (US); Kathleen Mary Douglas, Winter Park, FL (US)

(72) Inventors: David Byron Douglas, Winter Park, FL (US); Robert Edwin Douglas, Winter Park, FL (US); Kathleen Mary Douglas, Winter Park, FL (US)

( * ) Notice: Subject to any disclaimer, the term of this patent is extended or adjusted under 35 U.S.C. 154(b) by 0 days.

(21) Appl. No.: 17/120,109

(22) Filed: Dec. 12, 2020

Related U.S. Application Data

(63) Continuation of application No. 16/594,139, filed on Oct. 7, 2019, now Pat. No. 10,893,844, and a continuation-in-part of application No. 15/949,202, filed on Apr. 10, 2018.

(60) Provisional application No. 62/743,837, filed on Oct. 10, 2018.

(51) Int. Cl.
| | | |
|---|---|---|
| *A61B 6/00* | (2006.01) |
| *G06T 19/00* | (2011.01) |
| *G06T 7/00* | (2017.01) |
| *A61B 90/00* | (2016.01) |
| *A61B 6/02* | (2006.01) |
| *G06T 15/08* | (2011.01) |
| *G02B 27/01* | (2006.01) |

(52) U.S. Cl.
CPC ............ *A61B 6/5211* (2013.01); *A61B 6/025* (2013.01); *A61B 6/502* (2013.01); *A61B 90/39* (2016.02); *G02B 27/017* (2013.01); *G06T 7/0014* (2013.01); *G06T 15/08* (2013.01); *G06T 19/006* (2013.01); *A61B 2090/3904* (2016.02); *G06T 2207/10112* (2013.01); *G06T 2207/10124* (2013.01); *G06T 2207/20036* (2013.01); *G06T 2207/30068* (2013.01)

(58) Field of Classification Search
CPC .......... G06T 7/0012; G06T 7/00; A61B 6/02; A61B 1/00; A61B 5/00; H04N 13/00; G02B 27/017
See application file for complete search history.

(56) References Cited

U.S. PATENT DOCUMENTS

2012/0212398 A1* 8/2012 Border .................... G06F 3/013
                                                            345/8
2017/0336631 A1* 11/2017 Armstrong ........... G02B 27/017

FOREIGN PATENT DOCUMENTS

WO    WO-2019152617 A1 *  8/2019  ........... G02B 27/017

* cited by examiner

*Primary Examiner* — Ross Varndell

(57) ABSTRACT

A method for improved 3D imaging of a volume is disclosed. The application discussed is improved assessment of complex 3D structures including breast microcalcifications and incorporation of geo-registered tools. The 3D imaging is displayed on a geo-registered head display unit.

14 Claims, 13 Drawing Sheets

FLOW DIAGRAM OF GENERATING 3D VOLUMETRIC DATASET FROM A TOMOSYNTHESIS DATASET AND USING THIS DATASET FOR ENHANCED VIEWING

Record precise geometry of the digital breast tomosynthesis equipment. 100

↓

Prior to commencing digital tomosynthesis exam, option to affix pin head size radiographically detectable markers on the surface of the patient's breast. 101

↓

Perform digital breast tomosynthesis examination and collect data. 102

↓

Download DTS data into the 3D processing system along with associated meta data for particular DTS System including resolution, arc degrees, # images taken. 103

↓

Create a grid and associated X, Y, Z coordinate system, which is consistent with the DTS system resolution and subtends the volume subtended by the pin head radiographically detectable markers. 104

↓

Run the mathematical process to convert the multiple 2D DTS images into a single 3D DTS dataset composed of voxels with each voxel having a unique (x, y, z) coordinate
105

↓

Plot the 3D DTS data in the X, Y, Z coordinate system. 106

↓

Display the 3D DTS data in true stereoscopic via the Extended Reality headset for radiologist examination. 107

↓

Computer responds to radiologist commands issued via the control unit to invoke the following: establishing view point; rotating, zooming, flying through the 3D volume and/ or adding false color to denote selected tissue types; invoking tissue filtering to reduce occulsoin of microcalcifiction and/ or tumerous tissue; creation of a 3D cursor and movement thereof to regions of interest and re-size/ re-shape, as desired; remove tissue external to 3D cursor, as desired; positioning the focal point pen to tissue of interest and create symbols/ notes, as desired; move contents of 3D cursor to geo-registered pedestal and affix contents to hand held pedestal; and, move hand held pedestal with affixed contents, as desired. View the reconstructed 3D dataset via standard slice-by-slice scrolling or via advanced imaging techniques.
108

Figure 1

OVERVIEW OF THE APPARATUS FOR IMPLEMENTING THE PROCESS OF FIGURE 1

ILLUSTRATION OF GEOREGISTRATION POINTS AND GRID ON THE SKIN SURFACE OF THE BREAST

ILLUSTRATION OF MICROCALCIFICATION POSITION SHIFT DURING TOMOSYNTHESIS

GEOMETRY FOR COMPUTING COORDINATE OF A MICROCALCIFATION

EXAMPLE OF FILTERING OF VOXELS INSIDE AND OUTSIDE OF THE 3D CURSOR
Figure 6A
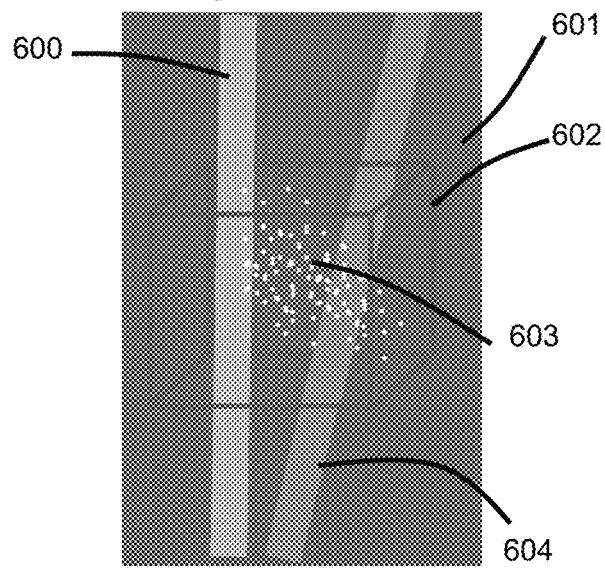
Figure 6B
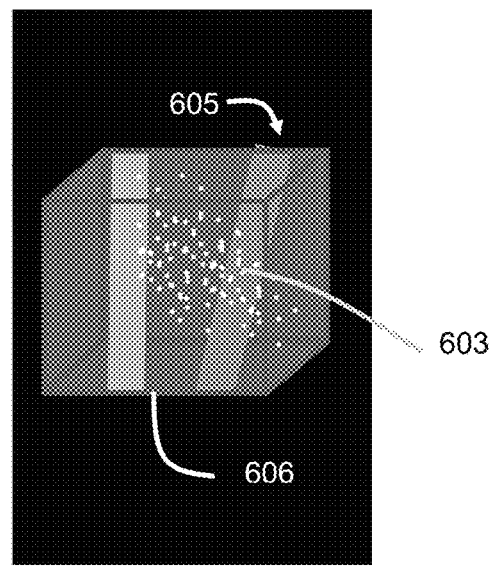
Figure 6C
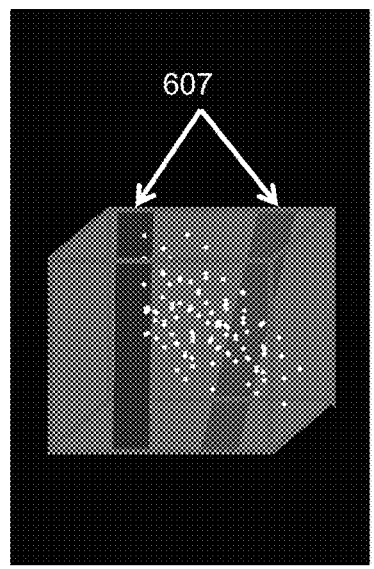
Figure 6D
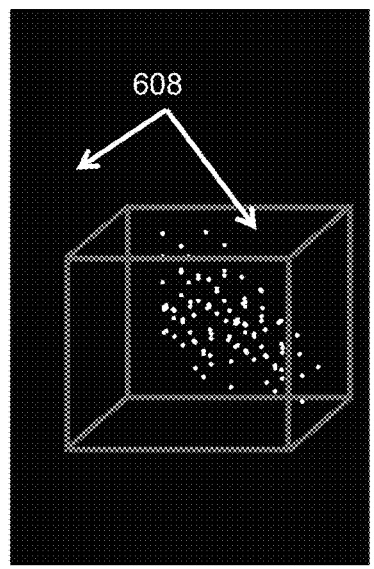
Figure 6

EXAMPLE VIEWING OF A CLUSTER OF MICROCALCIFICATIONS IN A 3D CURSOR WITH AN AUGMENTED REALITY HEAD DISPLAY UNIT

EXAMPLE USE OF GEOREGISTERED TOOLS IN COMBINATION WITH 3D CURSOR
Fig. 8A
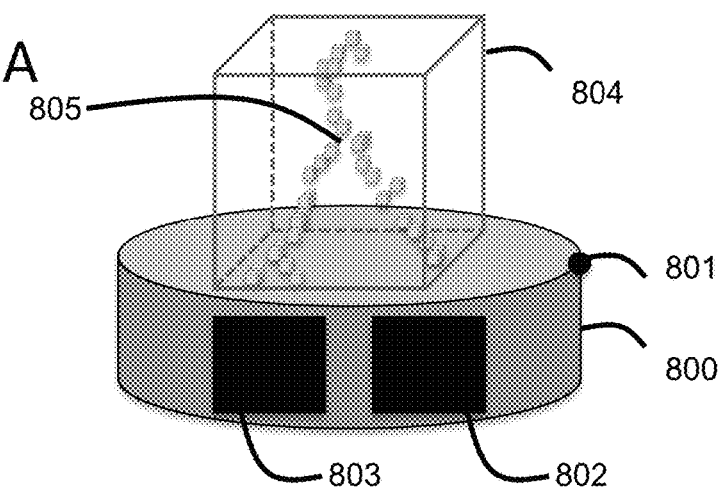
Fig. 8B
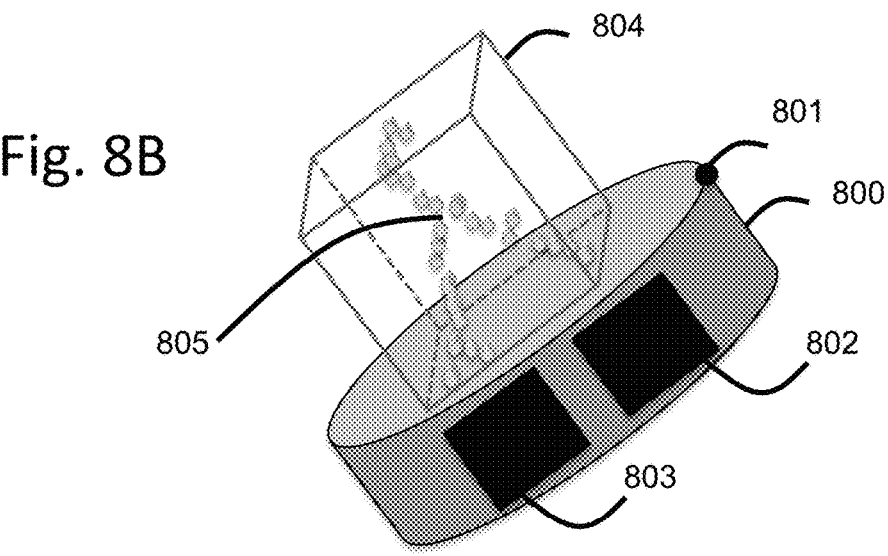
Fig. 8C
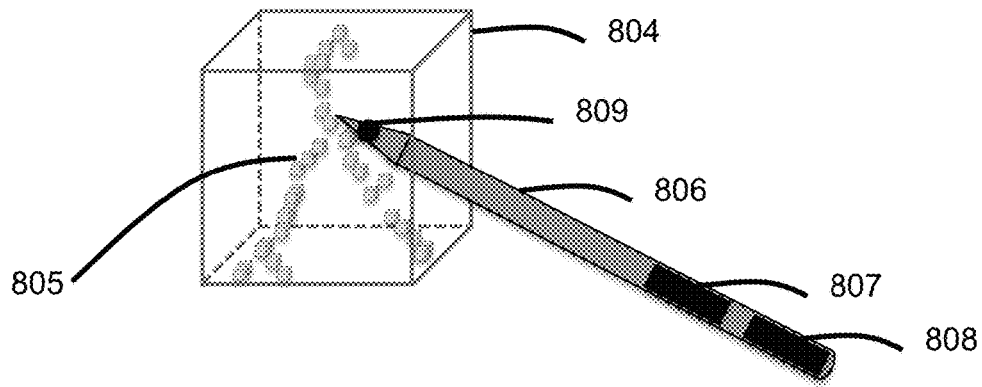
Figure 8

TOP DOWN VIEW OF MAMMOGRAPHER'S DESK ILLUSTRATING SEVERAL
OF THE TOOLS WITH POSITION AND ORIENTATION TRACKING

DIGITAL BREAST TOMOSYNTHESIS UNDER VARYING COMPRESSIONS
Case 1
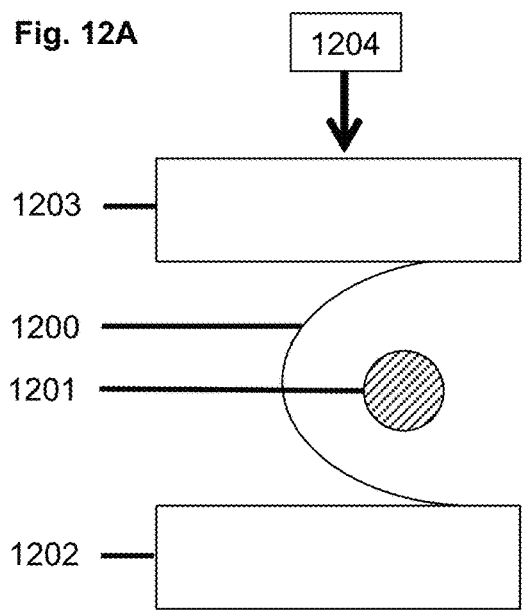
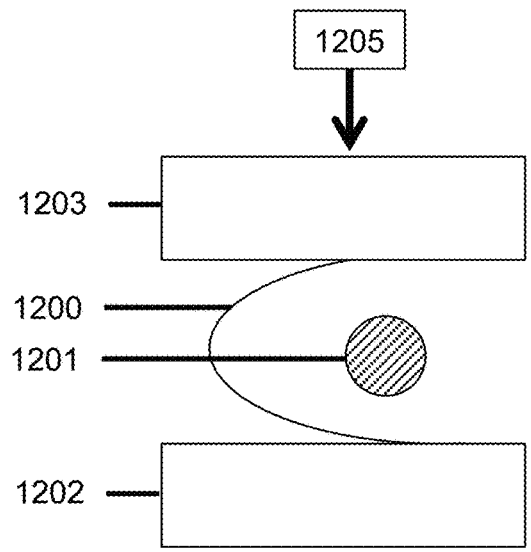
Case 2
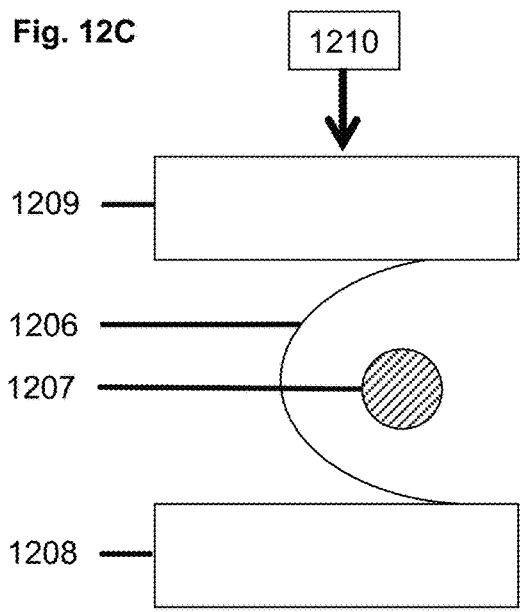
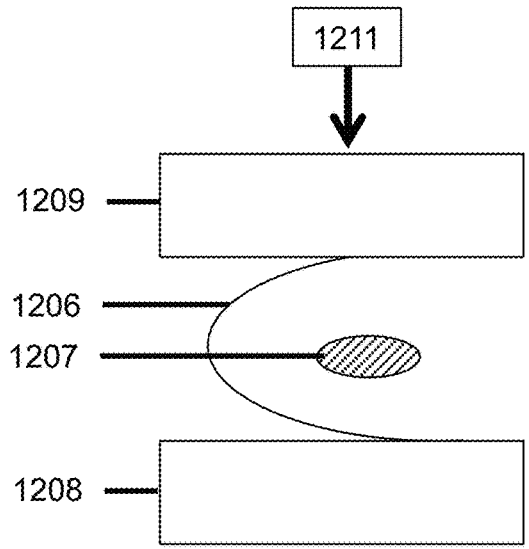
Figure 12

ENHANCED VOLUME VIEWING

CROSS-REFERENCES TO RELATED APPLICATIONS

The present application is a continuation of U.S. patent application Ser. No. 16/594,139 filed on Oct. 7, 2019, which claims the benefit of U.S. Provisional Application 62/743,837 filed on Oct. 10, 2018. The present application is also a continuation-in-part of U.S. patent application Ser. No. 15/949,202 filed on Apr. 10, 2018.

TECHNICAL FIELD

Aspects of this disclosure are generally related to radiological imaging, and more particularly to 3D breast imaging.

BACKGROUND

An improved type of mammogram to detect breast cancer is referred to as 3D mammogram. A better description is digital breast tomosynthesis (DBT). DBT differs from a common mammogram in that with DBT, the X-ray machine sweeps out an arc taking multiple X-rays while the breast is compressed by a paddle against the X-ray detector plate whereas a standard mammogram takes two X-ray of the compressed breast from the vertical and oblique angles. Thus, the DBT process takes X-ray pictures from more angles and in this process, there are fewer false positives (of cancer) and fewer call backs for additional evaluation are reduced saving costs to the medical system and angst of the part of the patient.

There is, however, a problem with both the DBT and the common mammogram. Specifically, neither process can reliably discern the patterns of microcalcifications within the breast—some of which are indicative of ductal carcinoma in situ (DCIS) and some of which are benign. In general, these microcalcifications may appear as a cluster, but it can be difficult to determine the exact 3D distribution of the cluster of microcalcifications. When one considers that the number of these microcalcifications typically ranges between as small as single digit up to 1000 or more, seeing all of these calcifications on a single or, multiple in the case of DBT, two dimensional arrays can present a major challenge to the radiologist to discern a branching structure which is suspicious for DCIS.

Known techniques for 3D viewing of medical images are described in U.S. Pat. No. 9,349,183, Method and Apparatus for Three Dimensional Viewing of Images, issued to Douglas, U.S. Pat. No. 8,384,771, Method and Apparatus for Three Dimensional Viewing of Images, issued to Douglas, Douglas, D. B., Petricoin, E. F., Liotta L., Wilson, E. D3D augmented reality imaging system: proof of concept in mammography. Med Devices (Auckl), 2016; 9:277-83, Douglas, D. B., Boone, J. M., Petricoin, E., Liotta, L., Wilson, E. Augmented Reality Imaging System: 3D Viewing of a Breast Cancer. J Nat Sci. 2016; 2(9), and Douglas, D. B., Wilke, C. A., Gibson, J. D., Boone, J. M., Wintermark, M. Augmented Reality: Advances in Diagnostic Imaging. Multimodal Technologies and Interaction, 2017; 1(4):29.

SUMMARY

All examples, aspects and features mentioned in this document can be combined in any technically possible way. All patents and patent applications referenced herein are incorporated by reference.

Aspects of the present disclosure include an improved process for evaluating the DBT data than looking at 2D image slices with a cloud of microcalcifications and/or tumorous tissue. In some implementations that improved process includes looking at a geo-registered 3D DBT volume by true stereoscopic viewing and the ability to rotate, zoom, and fly into this volume. This enables the medical person viewing the 3D DBT data to gain a thorough understanding of the underlying structure of the microcalcifications and/or tumorous tissue. Additionally, the breast is compressed in multiple different manners and the morphologic changes analyzed. Apparatus and methods by which this better way can be achieved are described herein.

Some implementations comprise geo-registration and display of digital tomosynthesis (DBT) data in three dimensions (3D). From the 2D DBT data a 3D volume will be created and presented to medical personnel in true stereoscopic images via an augmented reality/virtual reality (AR/VR) headset. Note that the images obtained during the digital tomosynthesis process are images with differing gray scales depending on the density of the tissue attenuated by the X-ray beam onto the detector array for each respective pixel of the array.

Some implementations comprise but, are not limited to, an apparatus comprised of a computer system which runs the mathematical process (described below) applied to the DBT data and generates stereoscopic images of 3D DBT data, a medical personnel control device (e.g., but not limited to a joy stick or game controller developed in accordance with U.S. Ser. No. 16/524,275 USING GEO-REGISTERED TOOLS TO MANIPULATE THREE-DIMENSIONAL MEDICAL IMAGES) from which commands are issued to change viewing points, rotate images, etc. (described below) and augmented reality (AR)/virtual reality (VR) headset which displays the 3D DBT data in true stereoscopic format. Further, some implementations will have a geo-registered focal point pen and a geo-registered pedestal.

Some implementations comprise, but are not limited to, a set of pin head sized radiodense surfaces (nominally eight) placed on the skin surface of each breast in a manner such that the majority of the tissue of the breast would be encased within the volume subtended by radiodense points. These pin head radiodense surfaces are affixed to the breast prior to commencing the DBT process and would have a unique signature when projected onto the DBT system detector array. This would be accomplished in accordance with procedures outlined in U.S. Ser. No. 16/509,592 IMPLANTABLE MARKERS TO AID SURGICAL OPERATIONS.

Some implementations comprise but, are not limited to, establishing a 3D grid system and associated X, Y, Z coordinate system with a resolution consistent with the digital tomosynthesis system on which the DBT data is collected. In accordance with this process, the tissue within the images generated by the digital tomosynthesis would be geo-registered within the grid system and associated X, Y, Z coordinate system. This grid would include multiple radiographically detectable markers. The individual markers could be made of the same or different size, shape, materials as desired to assist with geo-registration. A unique signature of a particular spot may be use to track a portion of the breast under a first and second configuration. Thus, the internal anatomic features can be registered to the external grid features.

Some implementations comprise, but are not limited to, establishing a mathematical process by which each of the microcalcifications and/or tumorous tissue could be geo-registered within the 3D grid system and associated X, Y, Z coordinate system. In this mathematical process, note that the X-ray for each of the X-ray pictures is approximated to be a point source. When the X-ray passes through the microcalcification and/or tumorous tissue, the X-ray beam is partially attenuated and is projected onto the detector array (i.e., the microcalcification and/or tumorous tissue will have a specific X-coordinate and a specific Y-coordinate on the detector array). These microcalcifications and/or tumorous tissue specific X-coordinates and a specific Y-coordinates will change as the X-ray machine progresses through the arc and subsequent X-ray pictures are taken. First consider the X-ray machine in the vertical position over the breast and a single microcalcification in the center of the breast. The projection of this microcalcification onto the detector array would be in the center of the detector array. If the microcalcification were located off of the center line, the projection of this microcalcification on the detector array would be based on the angle from the X-ray tube through the X-coordinate, Y-coordinate and Z-coordinate of the microcalcification and onto the detector array. As the X-ray machine moves to a new position and takes the next X-ray, the microcalcification will have a new X-coordinate and a new Y-coordinate on the detector array. By back plotting a line at the angle from the first X-coordinate and Y-coordinate to the point of emission of the X-ray and next back plotting the line at the angle from the second X-coordinate and second Y-coordinate to the point of emission of the X-ray, these two lines will intersect at the X-coordinate, Y-coordinate and Z-coordinate of the microcalcification. This process would be repeated multiple times for each of the X-rays within the DBT examination and with these further calculations, the estimate of X-coordinate, Y-coordinate and Z-coordinate of the microcalcifications can be refined. Given that the X-coordinate, Y-coordinate and Z-coordinate of the microcalcification are calculated and object to image distance is known, this process would also be able to correct for magnification, focal spot blurring and motion blurring.

Some implementations comprise, but are not limited to, establishing (i.e., plotting digitally) the locations of the microcalcifications, normal breast tissue, blood vessels, and/or tumorous tissue discovered in the above mathematical process in the grid system with their respective X, Y, Z coordinates.

In some implementations, the medical personnel could select viewing options via the control unit.

Some implementations comprise, but are not limited to, a process by which the 3D DBT data can be viewed. Specifically, a view point, which can be modified during the course of the examination, will be established. From this view point two different images will be generated—one from the position of the left eye viewing point (LEVP) and a separate one for the right eye viewing point (REVP). These images will be projected on AR/VR headset. The 3D volume could: be rotated in any direction; zoomed in/out; false color could be added for DBT data with intensity indicative of microcalcification and/or tumorous tissue type tissue; and the viewing point could be modified and new images generated for the LEVP and REVP would be generated by these changes accordingly (U.S. Pat. No. 8,384,771, Method and apparatus for three dimensional viewing of images and U.S. Pat. No. 9,349,183, Method and apparatus for three dimensional viewing of images).

In some implementations, a 3D cursor would be generated in accordance with U.S. Pat. No. 9,980,691, Method and apparatus for three dimensional viewing of images and U.S. patent application Ser. No. 15/878,463, Interactive 3D cursor for use in medical imaging to assist medical personnel in viewing a sub-set of the DBT data. The 3D cursor could be changed in size and shape and moved within the 3D DBT volume to a location and orientation selected by the medical personnel via commands inserted to the computer (or interface to cloud computing) via the control unit. At the discretion of the medical person viewing the 3D DBT data, tissue external to the 3D cursor could be temporarily removed to improve viewing.

In some implementations, filtering of DBT data could be applied to the entire 3D volume or to a sub-set of data contained within the 3D cursor (U.S. patent application Ser. No. 15/904,092, INTERACTIVE VOXEL MANIPULATION STRATEGIES IN VOLUMETRIC MEDICAL IMAGING ENABLES VIRTUAL MOTION, DEFORMABLE TISSUE, AND VIRTUAL RADIOLOGICAL DISSECTION). This filtering could largely eliminate non-microcalcification and/or tumorous type tissue and reduce/eliminate occlusion of microcalcifications and/or tumorous type tissue for enhanced viewing by medical personnel.

In some implementations, a focal point pen would be generated and moved within the 3D DBT volume. The focal point pen could be used inter alia to: mark/trace the microcalcification and/or tumorous tissue structure. The focal point pen could create virtual symbols (e.g., arrows to structures of interest or virtual written notes of findings) to: facilitate discussions between medical personnel and/or medical personnel with patients; and assist in preparation of reports. The focal point pen would be generated in accordance with U.S. patent application Ser. No. 16/524,275 USING GEO-REGISTERED TOOLS TO MANIPULATE THREE-DIMENSIONAL MEDICAL IMAGES.

In some implementations, a geo-registered pedestal would be available for the medical personnel. In this implementation, the medical person could move the 3D cursor to a region of interest, re-size/reshape the 3D cursor to capture tissue of interest, and then move the contents to the geo-registered hand-held pedestal and affix the contents of the 3D cursor to the pedestal. This would enable the medical person closely examines the tissue as he/she moves their hand holding the pedestal and its contents. The geo-registered hand-held pedestal would be generated in accordance with U.S. patent application Ser. No. 16/524,275 USING GEO-REGISTERED TOOLS TO MANIPULATE THREE-DIMENSIONAL MEDICAL IMAGES.

In some implementations, given that the X-coordinate, Y-coordinate and Z-coordinate of the microcalcification are calculated and object to image distance is known, this process would also be able to correct for magnification, focal spot blurring and motion blurring.

Another implementation is performing compression at varying levels and generating a 3D dataset at each compression level. This would allow the radiologist to better understand how the tissues in the body change in relation to the changing pressures. This may help in determining whether a tumor is benign or malignant.

Some implementations comprise: a computer (or interface to cloud computing) which applies software to digital tomosynthesis medical images at the direction of medical personnel reviewing 3D medical images; a head display unit (or other type display which provides true stereoscopic imagery) that presents the geo-registered 3D DBT medical image(s); a geo-registered focal point pen that interacts with geo-registered 3D DBT medical images; a geo-registered pedestal/platform that interacts with geo-registered 3D DBT medical images; a geo-registration master control platform component interacts with other components and, in conjunction with geo-processing software would enable geo-registration of these components within the overall system containing the volumetric DBT medical images, and other system components; and, software for geo-registration of components within the system and generation of images to be displayed on the head display unit.

Some implementations comprise, but are not limited to, establishing (i.e., plotting digitally) the locations of the microcalcifications and/or tumorous tissue discovered in the above mathematical process in the grid system. This 3D DBT data would then be available for viewing via the head display unit.

Some implementations comprise, but are not limited to, master control platform functionality for medical personnel reviewing 3D DBT medical images to direct digital displays to be presented on the head display unit. This functionality includes that previously disclosed in U.S. Pat. No. 8,384,771, Method and apparatus for three dimensional viewing of images, U.S. Pat. No. 9,349,183, Method and apparatus for three dimensional viewing of images, U.S. Pat. No. 9,473,7166 Method and apparatus for three dimensional viewing of images, and U.S. Ser. No. 16/524,275 USING GEO-REGISTERED TOOLS TO MANIPULATE THREE-DIMENSIONAL MEDICAL IMAGES. These additional functions and associated commands may include, but are not limited to, the following functions to facilitate the examination of geo-registered 3D DBT medical images by medical personnel reviewing geo-registered 3D DBT medical images: when interfacing with the geo-registered 3D cursor, change the location and orientation of the cursor; invoke convergence; invoke filtering, segmentation, sequencing, statistical, and reporting operations; invoke geo-registration system consisting of: head mounted display with separate eyepiece displays for true stereoscopic displays; a geo-registered focal point pen; a geo-registered pedestal/platform; geo-registration to interact with the computer, in conjunction with geo-processing software which would enable geo-registration of these components within the overall system containing the volumetric 3D DBT medical images, and other system components; invoke movement options for: the head mounted display with separate eyepiece displays for true stereoscopic displays; a geo-registered focal point pen; a geo-registered pedestal/platform; in conjunction with geo-processing software which would enable geo-registration of these components within the overall system containing the volumetric 3D DBT medical images, and other system components; invoke a 3D cursor which would be geo-registered and moved within the coordinate system to volumes of interest/concern copy the volume and transport it to the pedestal for detailed examination; input the volume subtended by the 3D cursor into machine learning and artificial intelligence algorithms in accordance with PCT/US19/23968 RADIOLOGIST-ASSISTED MACHINE LEARNING WITH INTERACTIVE, VOLUME-SUBTENDING 3D CURSOR.

Some implementations may include a 3D cursor generated in accordance with U.S. Pat. No. 9,980,691 and U.S. patent application Ser. No. 15/878,463 to assist medical personnel in viewing a sub-set of the DBT data. The 3D cursor could be changed in size and shape and move within the 3D DBT volume to a location selected medical personnel via commands inserted to the computer via the control unit. At the discretion of the medical person viewing the 3D DBT data, tissue external to the 3D cursor could be temporarily removed.

Some implementations may comprise, but are not limited to, filtering of 3D DBT data: applied to the entire 3D volume or; to a sub-set of data contained within the 3D cursor (See U.S. patent application Ser. No. 15/904,092, Processing 3D medical images to enhance visualization). This filtering could largely eliminate non-microcalcification type tissue and eliminate occlusion of microcalcifications for enhanced viewing by medical personnel.

Some implementations comprise a focal point pen. The focal point pen could be used inter alia to: mark/trace the microcalcification and/or tumorous tissue structure. The focal point pen could create virtual symbols (e.g., arrows to structures of interest or virtual written notes of findings) to: facilitate discussions between medical personnel and/or medical personnel with patients; and assist in preparation of reports. The focal point pen would be generated in accordance with U.S. Ser. No. 16/524,275, USING GEO-REGISTERED TOOLS TO MANIPULATE THREE-DIMENSIONAL MEDICAL IMAGES.

Some implementations comprise a hand held geo-registered pedestal would be generated to mount the contents of the 3D cursor to facilitate examination 3D DBT results of the breast by medical personnel in accordance with U.S. patent application Ser. No. 16/524,275, USING GEO-REGISTERED TOOLS TO MANIPULATE THREE-DIMENSIONAL MEDICAL IMAGES.

Some implementations comprise, but are not limited to, implementation of functionality in viewing the 3D DBT data. The medical personnel could select viewing options via the control unit. These options would include but, are not limited to: selection of viewing points; rotation of the 3D DBT data; zooming into the 3D DBT data; addition of false color to certain types of tissue bases on its intensity; flying into the 3D DBT volume. The entire volume can then be viewed stereoscopically or some subset of the data within the 3D cursor. The 3D cursor could be changed in size and shape and move within the 3D volume to a location or orientation selected medical personnel via commands inserted to the computer via the control unit. Filtering could be applied to reduce occlusion by non-microcalcification type tissue. The focal point pen could be used inter alia to: mark/trace the microcalcification structure; assist with eye tracking and focal point focusing; insert notes for to future reference to facilitate discussions between medical personnel and patients; and assist in report preparation. The contents of the 3D cursor could be moved and affixed to the hand held geo-registered pedestal.

Some implementations comprise, but are not limited to, software that implements the following: geo-registration of DBT data through establishing a 3D grid system and associated X, Y, Z coordinate system; the mathematical process to convert the 2D DBT data into a 3D volume; the plotting the 3D DBT data; the master control platform functionality; the process by which the 3D DBT data can be viewed; establishing the 3D cursor with associated functionality; the process by which the 3D DBT data can be filtered; establishing the geo-registered focal point with associated functionality; establishing the geo-registered pedestal with associated functionality; implementing the overall system functionality.

Some implementations comprise visualization and analysis of anatomic structures other than in the breast. For example, the same type analysis could be performed for soft tissue lesions elsewhere in the body. Alternatively, this same analysis process could be performed for other 3D imaging datasets for analysis, to include imaging of inanimate objects.

Some implementations comprise but, are not limited to applying different levels of pressure to compress the breast. This digital tomosynthesis method could include applying the standard pounds per square inch (psi) for the initial reading (inter alia for comparative purposes with previous tomosynthesis readings) and subsequently increasing the pressure by a step function increase for a secondary reading. A third (or more) step increases could also be applied. In a similar manner, the psi could be increased is a near continuous fashion with DTS application readings taken during the periods of time when the psi was being increases. Technique would be optimized, of course, to minimize motion artifact. Note that different types of breast tissue respond differently with differing levels of pressure: dense breast tissue does not compress as easily as breast tissue with a high fatty tissue content. Further, different tumor types compress and are distorted in a different manner under changes in external pressure. These different levels can assist with more accurate diagnoses.

Some implementations comprise, but are but limited to obtaining quantification/measurement of image data during the application of differing levels of psi. The methods of obtaining quantification/measurement image data include, but are not limited to the following: calculating the number of voxels contained in the volume subtended by the radio dense markers and length, width, and height data between radio dense markers; use of a 3D cursor(s) would be generated in accordance with U.S. Pat. No. 9,980,691, Method and apparatus for three dimensional viewing of images and U.S. application Ser. No. 15/878,463, Interactive 3D cursor for use in medical imaging to assist medical personnel in viewing the DTS data to encase the tumor(s) and calculating the number of voxels contained in the 3D cursor(s); volume (note that the segmentation and filtering process of U.S. Pat. No. 8,384,771, Method and apparatus for three dimensional viewing of images could be used to eliminate non-tumor tissue contained within the 3D cursor(s); and measurements of distortion of the tumor size and shape.

BRIEF DESCRIPTION OF FIGURES

FIG. 1 is a flow diagram that illustrates a process of generating 3D volumetric dataset from a digital breast tomosynthesis dataset and using this dataset for enhanced viewing.

FIG. 6A illustrates an artery, a vein, breast tissue, microcalcifications, and a 3D cursor.

FIG. 6B illustrates filtering (i.e., subtraction) of the tissues external to the 3D cursor.

FIG. 6C illustrates changing the transparency of the tissues within the 3D cursor.

FIG. 6D illustrates filtering (i.e., subtraction) of all tissues both inside and external to the 3D cursor with the exception of the breast microcalcifications.

FIG. 8A illustrates the 3D cursor affixed to a geo-registered platform.

FIG. 8B illustrates tilting of the geo-registered platform.

FIG. 8C illustrates pointing to the microcalcifications inside of the 3D cursor with the geo-registered focal point pen.

FIG. 12A illustrates a low level of compression of the breast and a breast mass that is round in shape.

FIG. 12B illustrates a high level of compression of the breast and the breast mass remains round in shape.

FIG. 12C illustrates a low level of compression of the breast and a breast mass that is round in shape.

FIG. 12D illustrates a high level of compression of the breast and the breast mass becomes flattened.

DETAILED DESCRIPTION OF FIGURES

Figure 2:
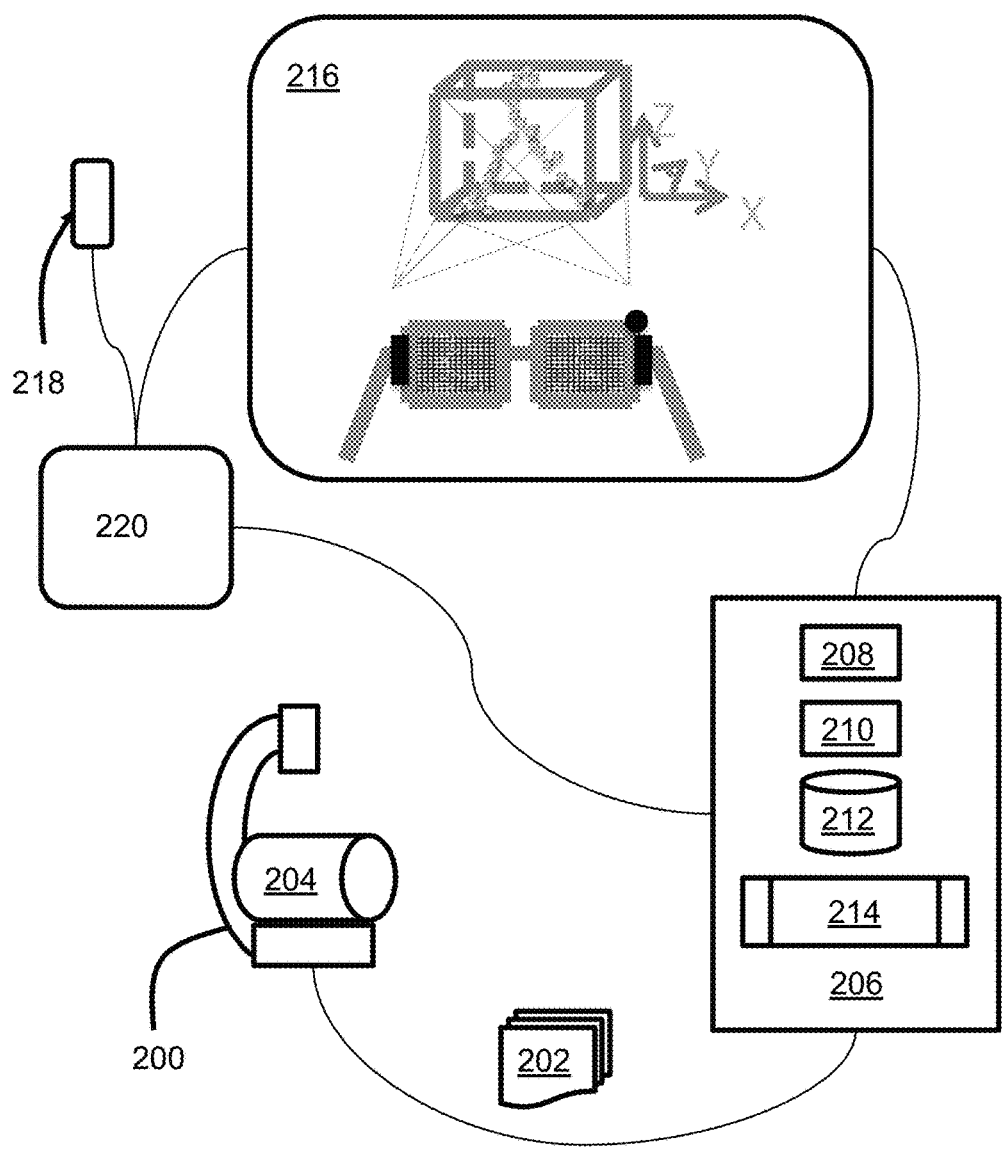
FIG. 2 illustrates an apparatus for implementing the process of FIG. 1.

FIG. 1 is a flow diagram that illustrates a process of generating 3D volumetric dataset from a tomosynthesis dataset and using this dataset for enhanced viewing. The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, Such as initialization of loops and variables and the use of temporary variables are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order. The first step 100 is to record precise geometry of the digital breast tomosynthesis equipment. The second step 101 is prior to commencing digital tomosynthesis exam, have the option to affix pin head size radiographically detectable markers on the surface of the patient's breast. The preferred option would be to have the mammography technologist place the markers, see U.S. patent application Ser. No. 16/509,592, IMPLANTABLE MARKERS TO AID SURGICAL OPERATIONS. The third step 102 is to perform digital breast tomosynthesis examination and collect data. Note that this can be performed under varying levels of compression of the breast. For example, a first 3D volume can be performed at a first level of compression of the breast. Then, a second 3D volume can be performed at a second level of compression of the breast. The fourth step 103 is to download DBT data into the 3D processing system along with associated meta data for particular DBT System including DBT system resolution, arc degrees, number of images taken. The fifth step 104 is to create a grid and associated X, Y, Z coordinate system which is consistent with the DBT system resolution and subtends the volume subtended by the pin head size radiographically detectable markers. The sixth step 105 is to run the mathematical process to convert the multiple 2D DBT images into a single 3D DBT dataset composed of voxels with each voxel having a unique (x, y, z) coordinate. The seventh step 106 is to plot the 3D DBT data in the X, Y, Z coordinate system. The eighth step 107 is to display the 3D DBT data in true 3D via an extended reality (e.g., augmented reality, mixed reality or virtual reality) headset for radiologist examination. The ninth step 108 is for the computer responds to radiologist commands issued via the control unit to invoke the following: establishing view point; rotating, zooming, flying through the 3D volume and/or adding false color to denote selected tissue types; invoking tissue filtering to improve visualization of microcalcifiction and/or tumerous tissue; creation of a 3D cursor and movement thereof to regions of interest and re-size/re-shape, as desired; remove tissue external to 3D cursor, as desired; positioning the focal point pen to tissue of interest and create symbols/notes, as desired; move contents of 3D cursor to geo-registered pedestal and affix contents to hand held pedestal; and, move hand held pedestal with affixed contents, as desired. View the reconstructed 3D dataset via standard slice-by-slice scrolling or via advanced imaging techniques including those described in U.S. Pat. No. 8,384,771, Method and apparatus for three dimensional viewing of images, U.S. Pat. No. 9,349,183, Method and apparatus for three dimensional viewing of images, U.S. Pat. No. 9,473,766, Method and apparatus for three dimensional viewing of images, U.S. Pat. No. 9,980,691, Method and apparatus for three dimensional viewing of images, U.S. patent application Ser. No. 15/904,092, Processing 3D medical images to enhance visualization, U.S. patent application Ser. No. 16/195,251, INTERACTIVE VOXEL MANIPULATION IN VOLUMETRIC MEDICAL IMAGING FOR VIRTUAL MOTION, DEFORMABLE TISSUE, AND VIRTUAL RADIOLOGICAL DISSECTION, U.S. patent application Ser. No. 16/524,275, USING GEO-REGISTERED TOOLS TO MANIPULATE THREE-DIMENSIONAL MEDICAL IMAGES, PCT/US19/47891, A VIRTUAL TOOL KIT FOR RADIOLOGISTS, U.S. patent application Ser. No. 16/509,592, IMPLANTABLE MARKERS TO AID SURGICAL OPERATIONS, U.S. patent application Ser. No. 16/563,985, METHOD AND APPARATUS FOR THE INTERACTION OF VIRTUAL TOOLS AND GEO-REGISTERED TOOLS, and PCT/US19/23968, RADIOLOGIST-ASSISTED MACHINE LEARNING WITH INTERACTIVE, VOLUME-SUBTENDING 3D CURSOR.

FIG. 2 illustrates an apparatus for implementing the process illustrated in FIG. 1. A radiologic imaging system 200 (i.e., digital breast tomosynthesis) is used to generate 2D medical images 202 of a breast 204. The 2D medical images 202 are provided to an image processor 206, that includes processors 208 (e.g., CPUs and GPUs), volatile memory 210 (e.g., RAM), and non-volatile storage 212 (e.g. HDDs and SSDs). A program 214 running on the image processor implements one or more of the steps described in FIG. 1. 3D medical images are generated from the 2D medical images and displayed on an IO device 216. The IO device may include an extended reality display (e.g., mixed reality, virtual reality or augmented reality headset), monitor, tablet computer, PDA (personal digital assistant), mobile phone, or any of a wide variety of devices, either alone or in combination. The IO device may include a touchscreen, and may accept input from external devices (represented by 218) such as a keyboard, mouse, joystick, and any of a wide variety of equipment for receiving various inputs. However, some or all the inputs could be automated, e.g. by the program 214.

Figure 3A:
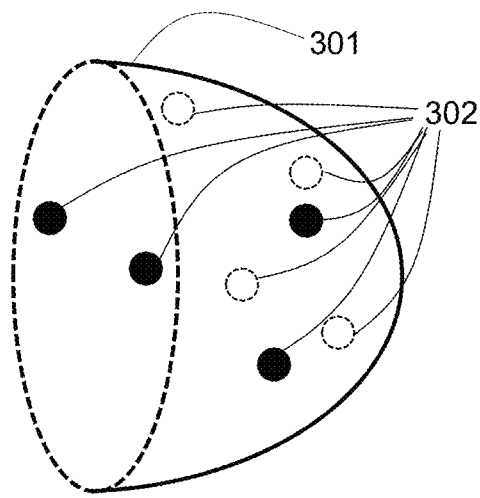
FIG. 3A illustrates the breast with georegistration points.
Figure 3B:
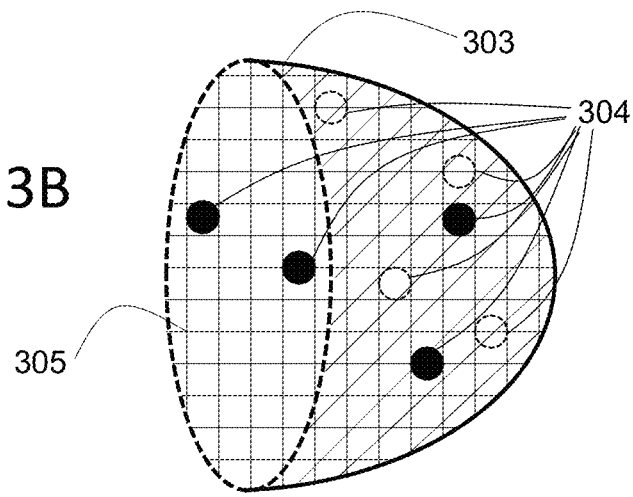
FIG. 3B illustrates the breast with georegistration points and a georegistration grid.
Figure 3C:
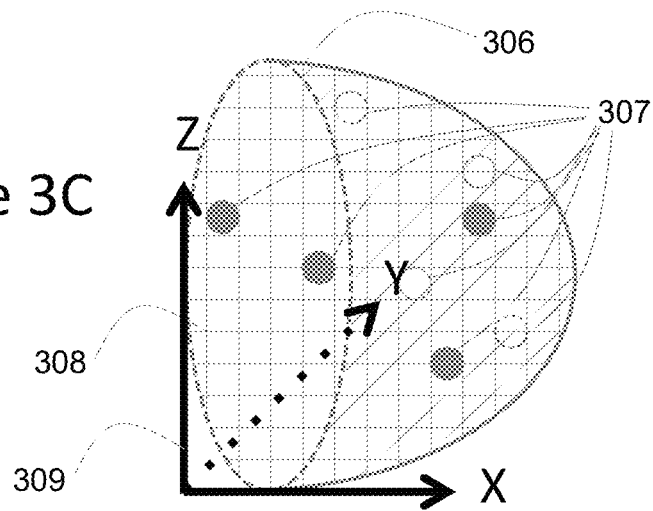
FIG. 3C illustrates the breast with georegistration points, georegistration grid and the coordinate system.

FIGS. 3A, 3B and 3C illustrate the breast with georegistration points on the skin surface, georegistration grid on the skin surface and coordinate system. FIG. 3A illustrates the breast 301 with georegistration points 302. FIG. 3B illustrates the breast 303 with georegistration points 304 and a georegistration grid 305. FIG. 3C illustrates the breast 306 with georegistration points 307, georegistration grid 308 and the coordinate system 309.

Figure 4A:
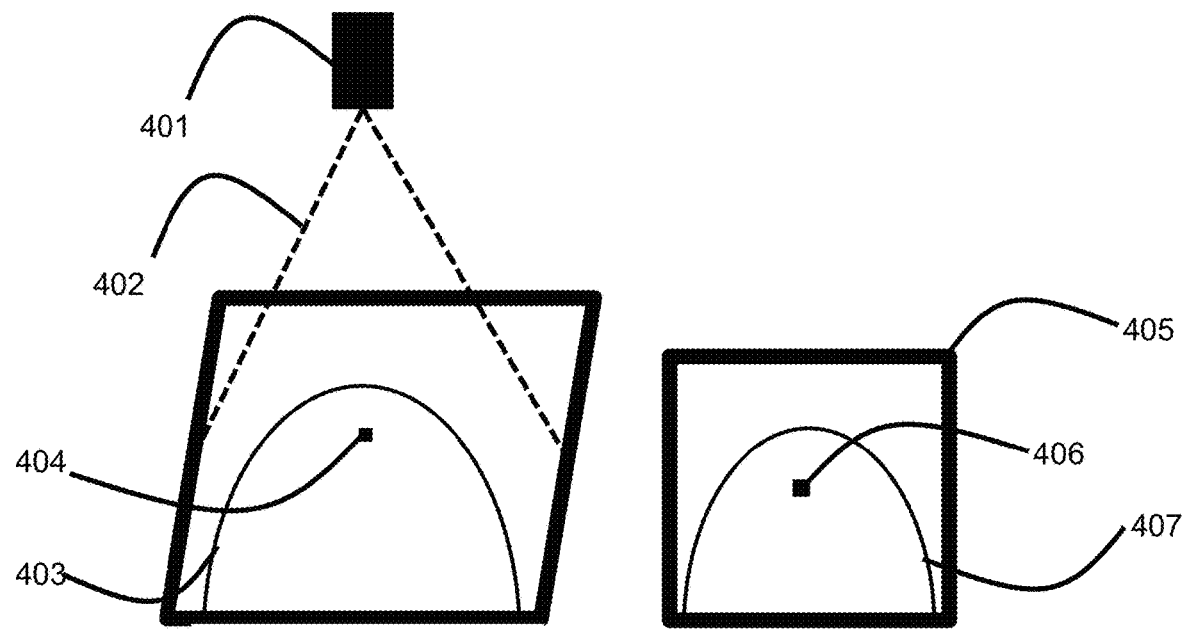
FIG. 4A illustrates an initial configuration of the X-ray detector, x-ray beam, breast, microcalcification within the breast, the detector and a first image.
Figure 4B:
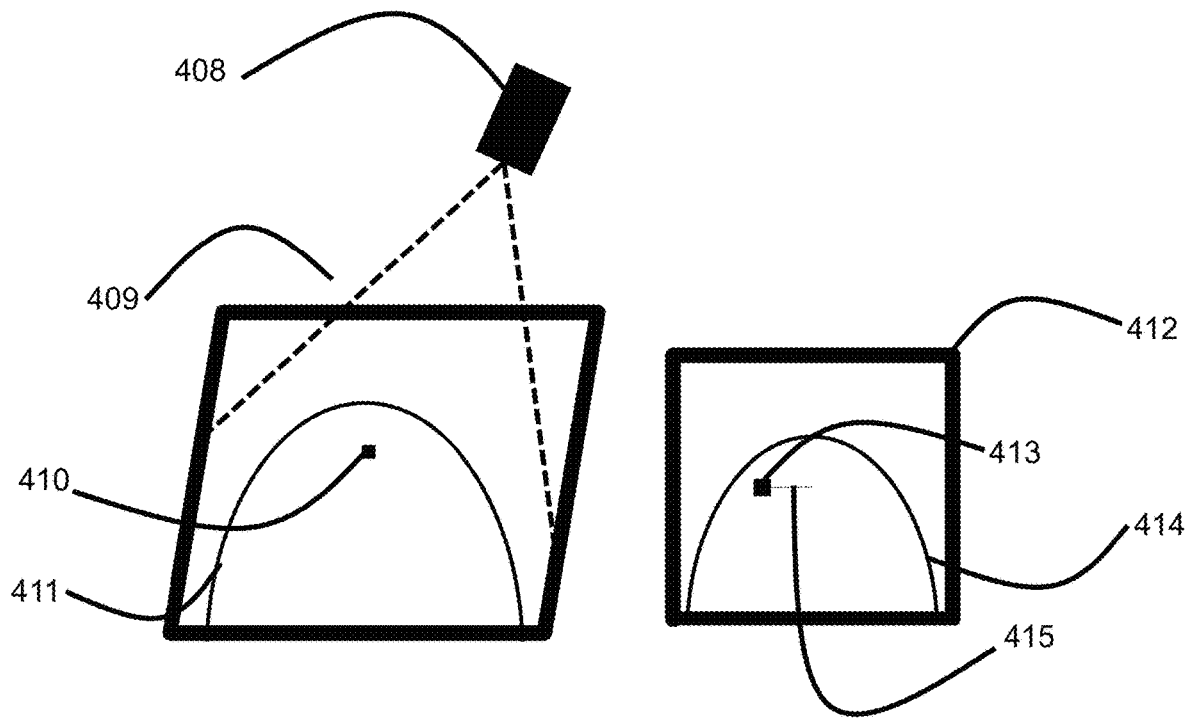
FIG. 4B illustrates movement of the X-ray detector and subsequent image.

FIGS. 4A and 4B illustrate the X-ray detector, x-ray beam, breast, microcalcification within the breast and the detector. In FIG. 4A, the x-ray tube is shown. The x-ray beam 402 is shown. The breast 403 is shown. 404 represents a microcalcification within the breast. 405 represents the image acquired. 406 represents the microcalcification within the image of the breast. 407 represents the image of the breast. In FIG. 4B, 408 represents the x-ray tube, which has been moved to a new position. 409 represents the x-ray beam from this new position. 410 represents the microcalcification in the breast, which has not moved. 411 represents the breast, which has also not moved. 412 represents the image acquired. 413 represents the image of the microcalcification, which has shifted in position as compared to 406 due to the new angle of the x-ray. 414 again demonstrates the image of the breast. 415 represents the distance that the microcalcification has shifted in image 412 as compared to image 405. Note that structures closer to the detector have less shift within the image than structures farther from the detector.

Figure 5A:
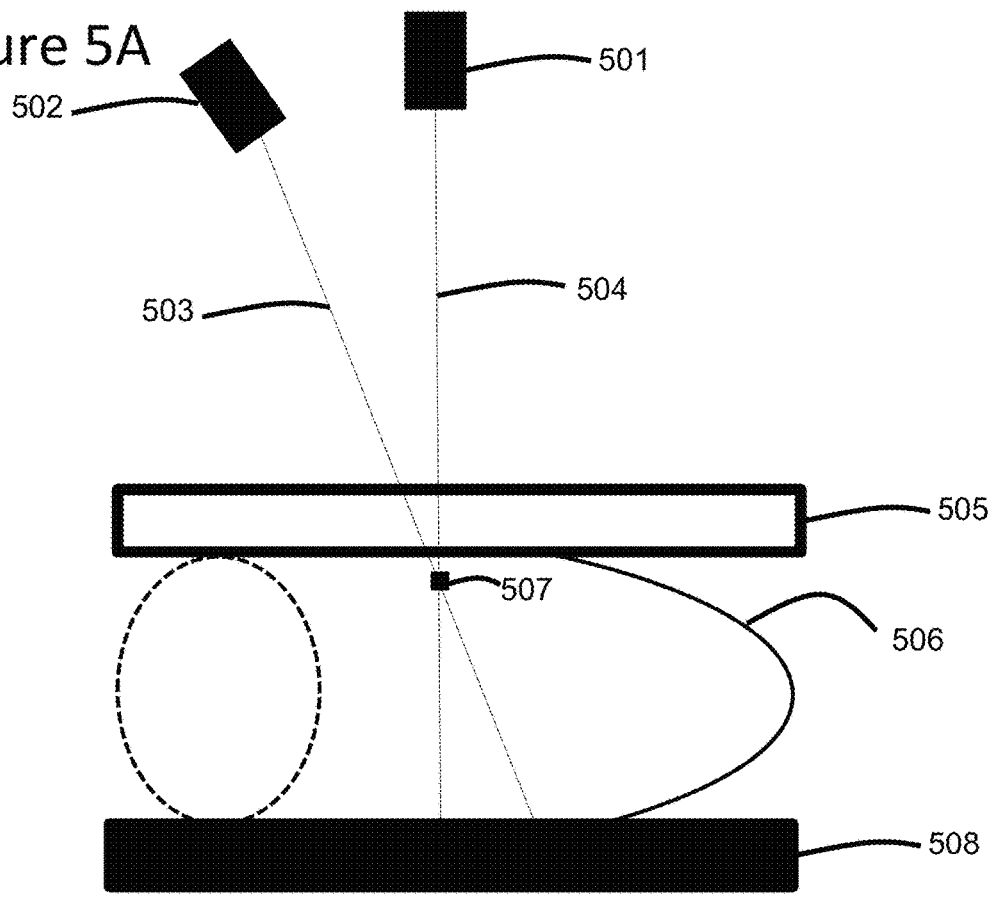
FIG. 5A illustrates the geometry of the X-ray tube, X-ray detector, compression paddle, breast and microcalcification.
Figure 5B:
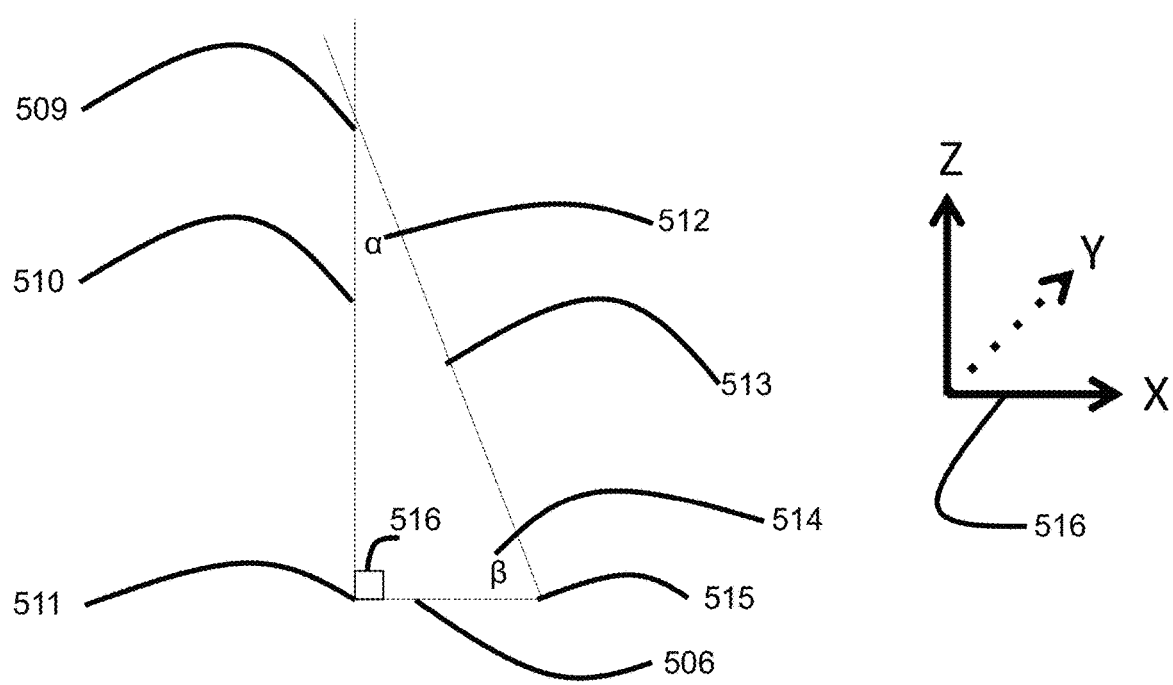
FIG. 5B illustrates the geometry of the microcalcification within the breast, the photon beams from the two X-ray tube positions, the X-ray detectors.

FIGS. 5A and 5B illustrate the geometry required to compute the (x, y, z) coordinate of a microcalcification. In FIG. 5A, the geometry of the X-ray tube, X-ray detector, compression paddle, breast and microcalcification are illustrated. 501 illustrates the x-ray tube at the initial position directly above the breast in a position to send x-rays are emitted vertically toward the floor. 502 illustrates the x-ray tube at a subsequent position in a position to send x-rays obliquely toward the floor. 503 illustrates the path of X-ray photons passing from the X-ray tube 502 through the microcalcification 507 and then to the detector 508. Similarly, 504 illustrates the path of X-ray photons passing from the X-ray tube 501 through the microcalcification 507 to the detector 508. 505 illustrates the paddle that compresses the breast, the properties of which have minimal X-ray attenuation. 506 is the patient's breast containing the microcalcification 507. In FIG. 5B, the geometry of the microcalcification within the breast, the photon beams from the two X-ray tube positions, the X-ray detectors is illustrated. 509 represents the location of the microcalcification, which will be assigned an (x, y, z) coordinate. The coordinate of the microcalcification of interest 509 is located at the intersection of the vertically oriented X-ray beam 510 and the obliquely oriented X-ray beam 513. The angle between the vertically oriented X-ray beam 510 and the obliquely oriented X-ray beam 513 is a 512. The spot where the vertically oriented X-ray beam hits the detector is 511. Note that the angle between the vertically oriented X-ray beam 510 and the detector is denoted as 516 and is 90 degrees. The spot where the obliquely oriented X-ray beam (from 502 and 503 in FIG. 5A) hits the detector is 515. The distance between the spot where the vertically oriented X-ray beam hits the detector 511 and the spot where the obliquely oriented X-ray beam hits the detector is 506. The angle between the detector, a portion of which is shown as 506, and the obliquely oriented X-ray beam 513 is β. To illustrate the calculation of the coordinates of the microcalcification from this geometry, the following assumptions will be made: 512 will be assumed to be 30 degrees; and, 506 will be assumed to be 2 cm. According to the law of a right triangle, angle β will equal 60 degrees. The tangent of 60 degrees equals the vertical height of the microcalcification in the z-direction divided by the distance 506. Therefore, the height of the microcalcification over the detector is √12 cm, which will be the z-coordinate of the microcalcification. The x-coordinate of the microcalcification is the spot on the detector from the vertically oriented X-ray beam 510. The y-coordinate of microcalcification is also the spot on the detector from the vertically oriented X-ray beam 510. X, Y, Z axes 516 are shown. For example, if a linear calcification is oriented vertically, on the image wherein the x-ray beam is vertically oriented with respect to the floor, the calcification would appear as a dot. If the x-ray beam is at an angle with respect to the calcification, then the calcification would appear as a line.

FIGS. 6A through 6D illustrate a cluster of microcalcifications within a volume-subtending 3D cursor with external tissues subtracted, transparency of internal structures altered and tissues both inside and outside of the 3D cursor subtracted except for the cluster of microcalcifications. In FIG. 6A, 600 illustrates an artery. 601 illustrates the breast tissue. 602 illustrates the 3D cursor. 603 illustrates a cluster of microcalcifications. 604 illustrates a vein. In FIG. 6B, note that the tissues external to the 3D cursor 605 have been subtracted. Note that the tissues inside of the 3D cursor 606 are unchanged from FIG. 6A. In FIG. 6C, the items shown are the same as FIG. 6B with the exception that the transparency (or grayscale) of the artery and vein 607 is altered to improve visualization of the microcalcifications. Transparency can be performed in a variety of ways, such as sparse sampling of the voxels segmented to a particular structure. Alternatively, or additionally, the opacity level of a particular voxel can be altered. Alternatively, or additionally, prioritized volume rendering can be perform as described in U.S. Provisional Patent Application 62/846,770 A METHOD OF PRIORITIZED VOLUME RENDERING TO IMPROVE VISUALIZATION OF PRIORITIZED ITEMS WITHIN A 3D VOLUME. In FIG. 6D, all tissues both inside and outside of the 3D cursor 608 with the exception of the microcalcifications are eliminated. This overall effort aims to improve visualization of microcalcifications for a user wearing an extended reality headset. By rotating, zooming, tilting or turning one's head, converging, one can better visualize and understand the true 3D distribution of microcalcifications.

Figure 7A:
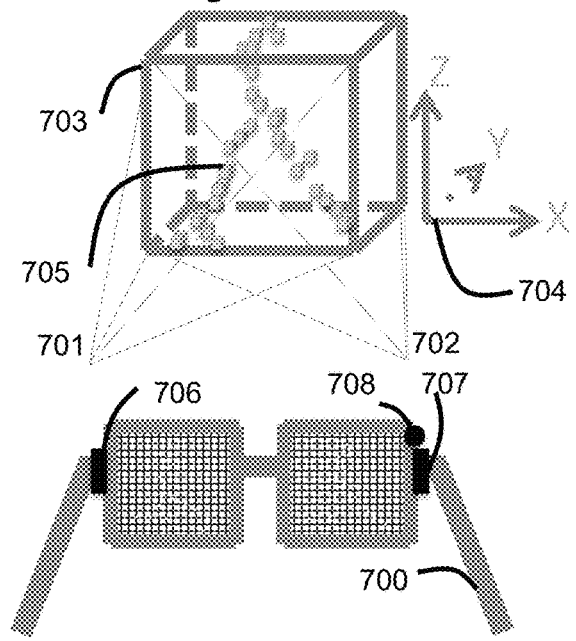
FIG. 7A illustrates the initial viewing perspective.
Figure 7B:
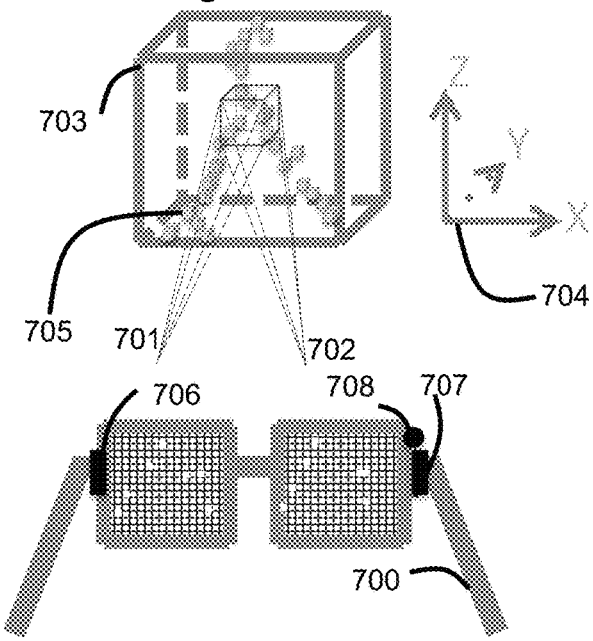
FIG. 7B illustrates changing the interocular distance and angular field of view.
Figure 7C:
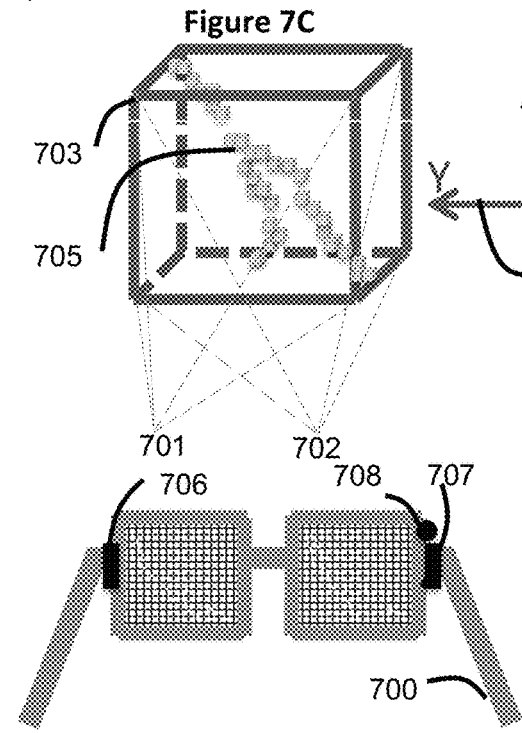
FIG. 7C illustrates the volume of interest (VOI) contained inside of the 3D cursor rotated 90 degrees.
Figure 7D:
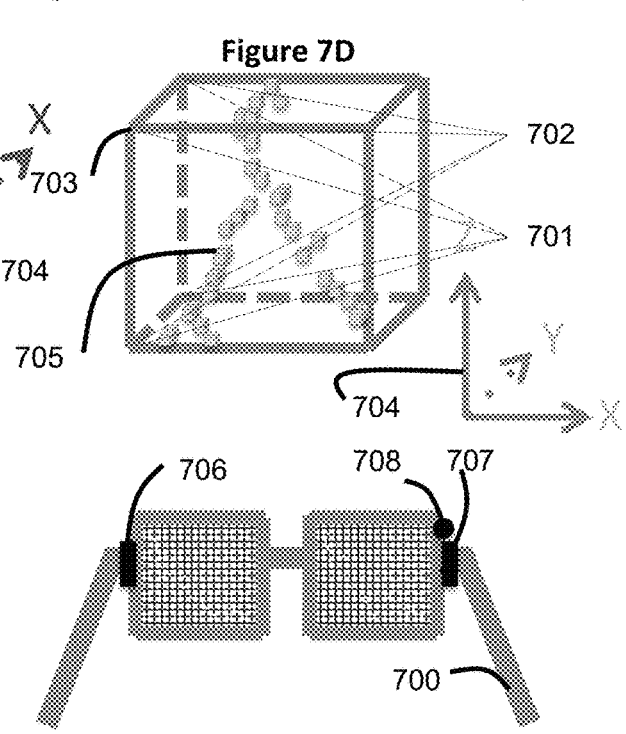
FIG. 7D illustrates changing the viewing perspectives by rotating it by 90 degrees.

FIGS. 7A through 7D illustrate viewing of the isolated cluster of microcalcifications using an augmented reality or virtual reality head mounted display. 700 illustrates the head display unit, which includes the transmit/receive element 706, the inertial measurement unit 707 and the georegistration point 708. 701 illustrates the left eye viewing perspective with left eye field of view. 702 illustrates the right eye viewing perspective with right eye field of view. 703 illustrates the 3D cursor. 704 illustrates the x, y, z coordinate system. 705 illustrates the microcalcifications. FIG. 7A illustrates the initial viewing perspective. FIG. 7B illustrates changing the interocular distance and angular field of view (compare with FIG. 7A). FIG. 7C illustrates the rotating the 3D cursor 90 degrees for a different viewing angle of the volume of interest (compare with FIG. 7A and FIG. 7B). FIG. 7D illustrates changing the viewing perspectives by rotating it by 90 degrees, such as looking at the cluster of microcalcifications from the side rather than from the front.

FIGS. 8A through 8C illustrate the use of the geo-registered platform and geo-registered focal point pen to inspect the microcalcifications within the 3D cursor. 800 illustrates the geo-registered platform. 801 illustrates a geo-registered point on the platform. 802 illustrates the transmit/receive element. 803 illustrates the inertial measurement unit. 804 illustrates the 3D cursor. 805 illustrates the microcalcifications within the 3D cursor. Note that the microcalcifications are shown as cubes for illustrative purposes only. In actuality, the microcalcifications may take on various shapes, sizes and densities. In FIG. 8A, the hand-held georegistration platform is affixed to the 3D cursor, which enables the mammographer to translate and rotate the georegistration platform and therefore view the 3D cursor and cluster of microcalcifications within the 3D cursor from multiple angles. In FIG. 8B, the hand-held georegistration platform is tilted and the 3D cursor and cluster of microcalcifications within the 3D cursor are likewise tilted. In FIG. 8C, the georegistered focal point pen 806 including the components of the transmit/receive element 807 and the inertial measurement unit 808 and the georegistered point 809 is shown pointing to the microcalcifications 805 within the 3D cursor 804. The georegistered pen can be used to perform functions such as image markup for communication with other physicians or areas of concern.

Figure 9:
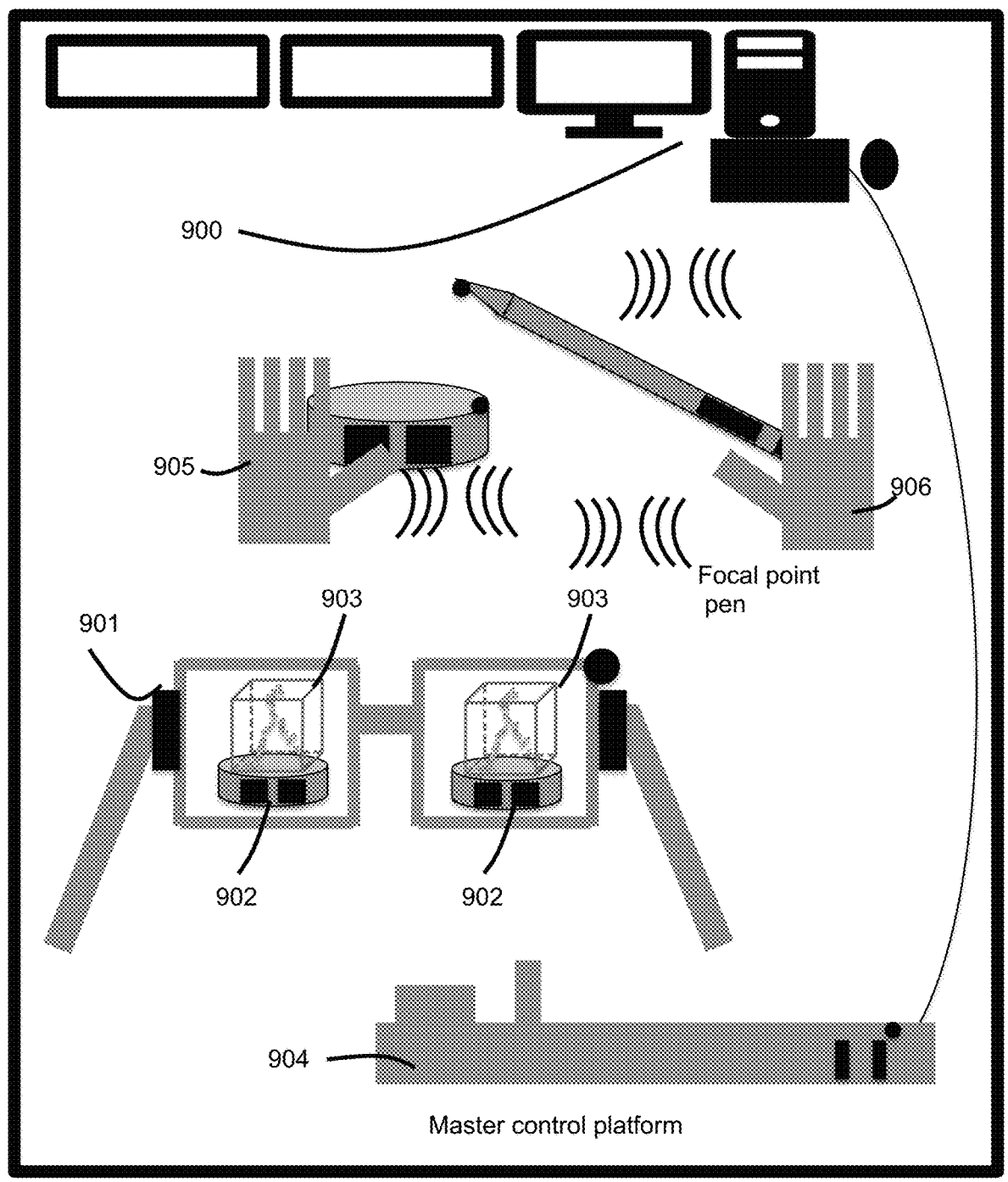
FIG. 9 illustrates a top down view of the mammographer's desk illustrating several of the tools with position and orientation tracking.

FIG. 9 illustrates a top down view of the mammographer's desk illustrating several of the tools with position and orientation tracking. 900 illustrates the standard equipment at the radiologists work station including multiple monitors, computer, power supply, mouse keyboard, voice dictation, etc. 901 illustrates the head display unit (HDU), such as an augmented reality, mixed reality or virtual reality system equipped with a transmit/receive element, an inertial measurement unit and a georegistration point. 902 illustrates the real-world image of the georegistered platform that the user can visualize with the HDU. 903 illustrates the virtual image of the 3D cursor displayed on the HDU, which includes the 3D cursor and a cluster of microcalcifications. 904 illustrates the master control platform used to guide the georegistration system. 905 illustrates the mammographer's left hand holding the georegistration platform, which is equipped with a transmit/receive element, an inertial measurement unit and a georegistration point. 906 illustrates the mammographer's right hand holding a focal point pen, which is equipped with a transmit/receive element, an inertial measurement unit and a georegistration point.

Figure 10:
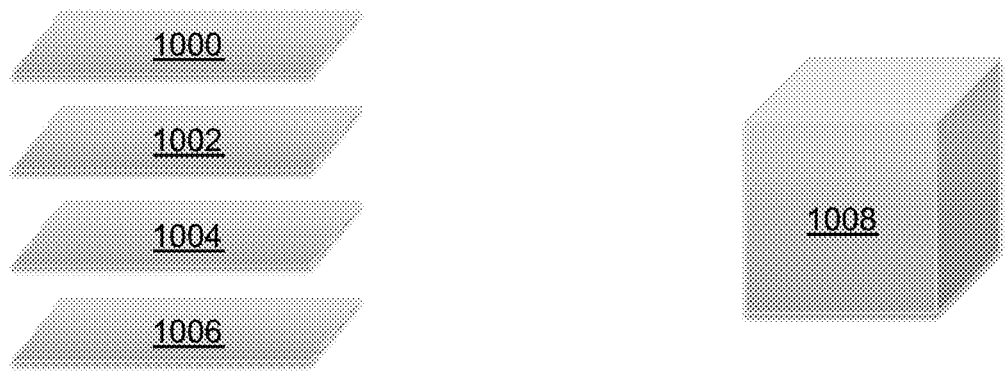
FIG. 10 illustrates the conversion of a digital breast tomosynthesis dataset into a single voxelated dataset.

FIG. 10 illustrates the conversion of a digital breast tomosynthesis dataset into a single voxelated dataset. 1000 illustrates a first digital breast tomosynthesis image from a first position of the x-ray tube. 1002 illustrates a first digital breast tomosynthesis image from a first position of the x-ray tube. 1004 illustrates a first digital breast tomosynthesis image from a first position of the x-ray tube. 1006 illustrates a first digital breast tomosynthesis image from a first position of the x-ray tube. 1008 illustrates a voxelated dataset. A series of pixels corresponding to calcifications would be detected on a first image 1000. From those pixels, a back projected image would be performed to the x-ray tube position. For each pixel with a calcification density, a set of potential x,y,z coordinates for the true location of the calcifications is yielded (i.e., along a line from the detector location to the x-ray tube). Next, a set of pixels corresponding to calcifications would be detected on a second image 1002. From those pixels, a back projected image would be performed to the x-ray tube position and a second set of potential x,y,z coordinates for the true location of the calcifications is yielded (i.e., along a line from the x-ray detector to the x-ray tube). The x,y,z coordinate of the calcification would be determined by the intersection point from the first tomosynthesis image to the second tomosynthesis image. This process would be repeated and a voxelated dataset formed for each pair of images. Note that multiple voxelated datasets could therefore be formed. Thresholds to plot only the calcifications could be set. Alternatively, thresholds to plot all tissues could be set.

Figure 11:
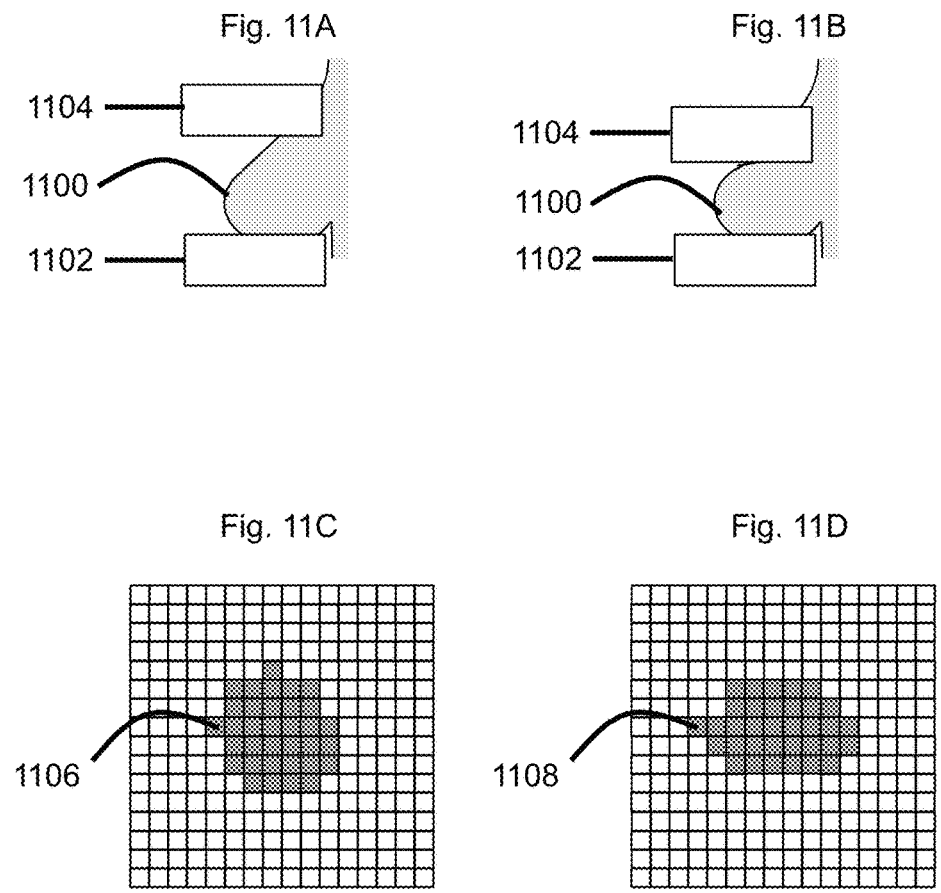
FIG. 11A illustrates a low pressure of compression of the breast.
FIG. 11B illustrates a high level of compression of the breast.
FIG. 11C illustrates an initial configuration of a breast mass.
FIG. 11D illustrates a subsequent configuration of a breast mass.

FIGS. 11A through 11D illustrate variable compression during digital breast tomosynthesis. The breast 1100 is shown. The detector 1102 is shown. The compression paddle 1104 is shown. FIG. 11A illustrates a low pressure of compression of the breast 1100. Note the initial contour of the breast 1100. FIG. 11B illustrates a high level of compression of the breast 1100. Note the subsequent contour of the breast 1100. FIG. 11C illustrates an initial configuration of a breast mass 1106. FIG. 11D illustrates a subsequent configuration of a breast mass 1108. Note that different tissues in the body will have different tissue type properties. For example, bone is rigid. Fat is easily deformable. Cancers can be hard. The purpose of doing the compression at two different levels is therefore to see how a lesion changes in its appearance and configuration under the two different conditions. This is accomplished by performing two different DBT examinations under different levels of compression, generating a 3D volume at the first level of compression, generating a 3D volume at the second level of compression and viewing the two datasets to see how the internal structures would change. For example, there might be two adjacent lesions and the radiologist is unsure whether these lesions are connected as a single bilobed mass or whether they are not connected at all. Such a technique can distinguish between these two scenarios. An optimum viewing strategy is to perform segmentation and then watch a segmented structure of interest change over the two (or more) configurations. Alternatively, compression could be performed from side-to-side under two (or more) compression levels. Sometimes there can be many lesions in a breast and it can be difficult for the radiologist to determine which lesion on the top-compression view corresponds to which lesion on the side-compression view. This is where the skin markers may be of benefit. By utilizing skin markers, the internal structures can be better analyzed. For example, there could be four areas in the breast of interest to the radiologist. The radiologist could place a 3D cursor over the first area of concern and then view it under various external compression settings to determine how it changes. Then perform a similar process to the second lesion and so on. An alternative approach to DBT for breast imaging is breast MM. In this case, a dynamic compression device can be built and synchronized with the breast MRI acquisition such that multiple volumes are obtained. For example, during a first time period at a first compression level, a first volume is built. During a second time period at a second compression level, a second volume is built. And, so on. The volumes can be viewed in a dynamic fashion on an extended reality display. Ideally, at least in some implementations, this would be performed with a fast acquisition MM. For example, a round mass might stay round even under dramatically different compression levels and this may indicate the hardness of the tumor and serve as an indicator for a first type of tumor (e.g., cancer risk). Alternatively, a round mass might become flattened into a pancake-like shape under a high amount of compression and this may indicate that the tumor is soft and serve as an indicator for a different type of tumor. Dynamic compression devices can be subsequently designed and built to accommodate the process outlined in this patent. Still further, the change in configuration of an anatomic feature can be utilized to help assign a tissue-type property (e.g., hardness). For example, a sphere shaped structure that remains sphere shaped despite a high pressure exerted upon it would be assigned a hard tissue-type property. In contrast, a sphere shaped structure that becomes pancake shaped when the same high pressure is exerted upon it would be assigned a soft tissue-type property. This is further described in U.S. patent application Ser. No. 15/904,092, INTERACTIVE VOXEL MANIPULATION STRATEGIES IN VOLUMETRIC MEDICAL IMAGING ENABLES VIRTUAL MOTION, DEFORMABLE TISSUE, AND VIRTUAL RADIOLOGICAL DISSECTION. Alternatively, this process could be performed in applications other than the breast. For example, a 3D imaging examination of the knee joint could be performed at a first configuration wherein the knee is in a straight 180 degree position. Then, a 3D imaging examination of the knee joint could be performed at a second configuration wherein the knee is slightly flexed to a 135 degrees position. Then, a radiologist wearing an extended reality head display unit can view the anatomic feature of the knee joint under different configurations and analyze changes therein. For example, a small meniscal tear can be obscured in the first 180 degree extended position, but then identified when the knee is in a 135 degree flexed position. MM coils can be manufactured to accommodate these changes in positions and optimize imaging parameters. In addition to the analysis of motion of joints, this process could be performed to analyze other structures that move in the body. The higher number of volumes would allow an improved ability to assess changes in configuration and would yield a more accurate analysis. For example, this process can be applied to an vascular structure whose configuration changes over the cycles of systole and diastole. For example, this process could be performed on the brain whose configuration changes over the cycles of CSF pulsation. For example, this process could be performed on the trachea or airways whose configuration changes over the cycles of inhalation and exhalation. The human body is mobile; thus, virtually every structure in the human body would be better analyzed during the 3D analysis of motion, changes in configuration and deformation as described in processes outlined in this patent.

FIGS. 12A through 12D illustrate two cases of tumors of varying hardness levels. FIG. 12A illustrates case 1 with a low level of compression. The breast 100, breast mass 1201, detector 1202, compression device 1203 and an initial pressure 1204 (e.g., with units of PSI) is illustrated. Note the configuration of the breast 1200 is somewhat round and the configuration of the mass 1201 is round. FIG. 12B illustrates case 1 with a high level of compression. The breast 1200, breast mass 1201, detector 1202, compression device 1203 and an subsequent higher pressure 1205 (e.g., with units of PSI) is illustrated. Note the configuration of the breast 1200 is now more flattened (compare with FIG. 12A) and the configuration of the mass 1201 is still round. This would indicate that the mass 1201 is hard. A deformability index could be established to indicate the amount of deformation of a given tissue in relation to the amount of pressure. FIG. 12C illustrates case 2 with a low level of compression. The breast 1206, breast mass 1207, detector 1208, compression device 1209 and an initial pressure 1210 (e.g., with units of PSI) is illustrated. Note the configuration of the breast 1206 is somewhat round and the configuration of the mass 1207 is round. FIG. 12D illustrates case 2 with a high level of compression. The breast 1206, breast mass 1207, detector 1208, compression device 1209 and an subsequent higher pressure 1211 (e.g., with units of PSI) is illustrated. Note the configuration of the breast 1206 is now more flattened (compare with FIG. 12C) and the configuration of the mass 1207 is still flattened. This would indicate that the mass 1201 is soft and deformable. A deformability index could be established to indicate the amount of deformation of a given tissue in relation to the amount of pressure. Note the deformability index of the breast mass 1201 in case 1 would be different from the deformability index of the breast mass 1207 in case 2. Note that in this illustration, two compression levels are illustrated. A 3D breast imaging examination would be performed at each of the two compression levels. Note that additional 3D imaging examinations could be performed at varying compression levels (e.g., 0.5 psi, 1.0 psi, 1.5 psi, 2.0 psi, 2.5 psi, 3.0 psi, 3.5 psi, 4.0 psi, etc.). The volumes will be reconstructed and viewed on an extended reality head display unit.

Figure 13:
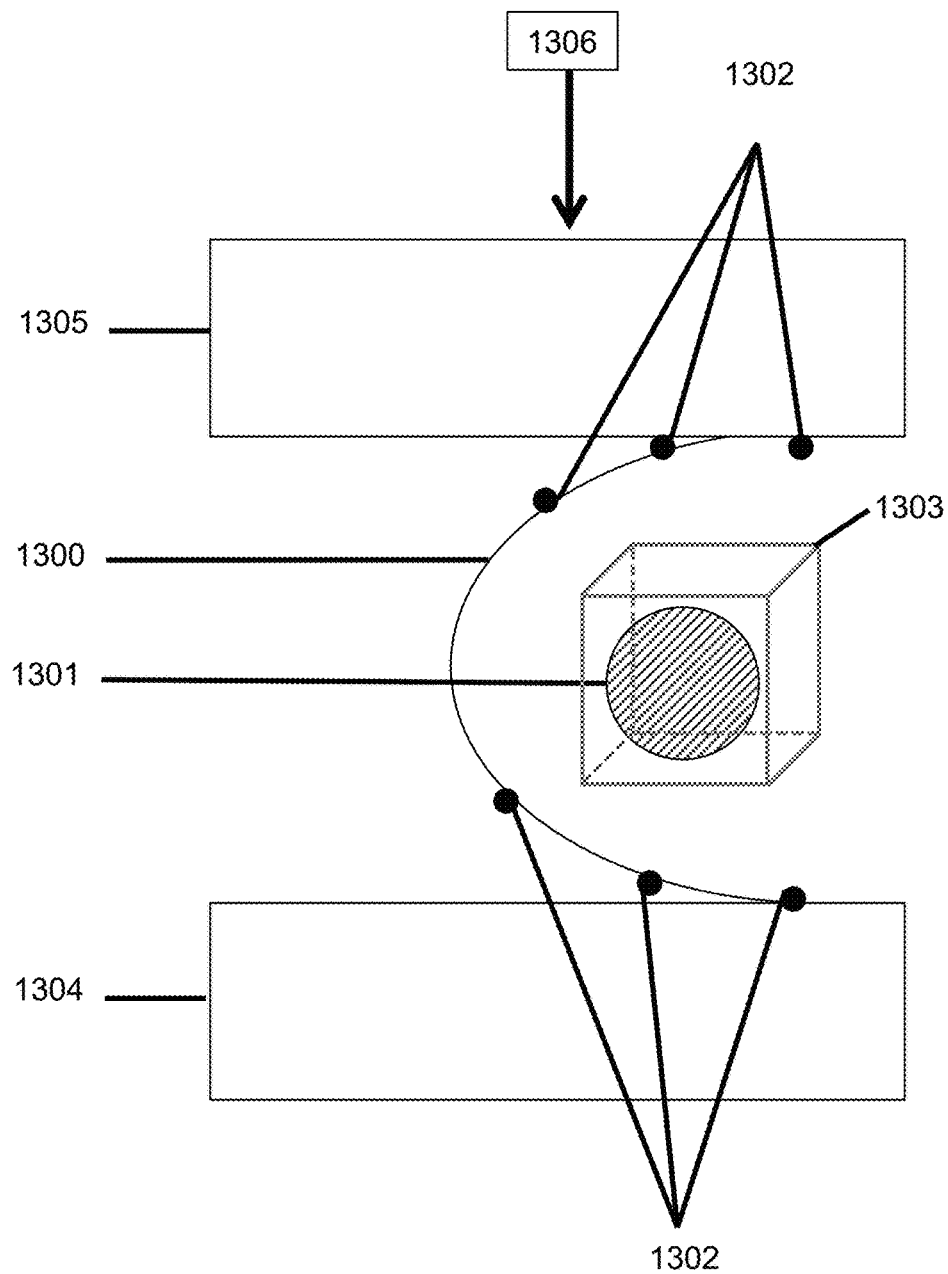
FIG. 13 illustrates a digital breast tomosynthesis dataset performed with skin markers.

FIG. 13 illustrates a digital breast tomosynthesis dataset performed with skin markers. The breast 1300, breast mass 1301, skin radioopaque markers 1302, detector 1304, compression device 1305 with adjustable compression 1306 are shown. The 3D cursor 1303 can be viewed on the image processing workstation. The remainder of the elements of a digital breast tomosynthesis machine is not shown. Note that the skin markers can be utilized as landmarks and reference points to improve understanding of how internal structures change. Note that this is especially important with less 3D imaging volumes obtained.

What is claimed:

1. A display unit comprising:
a processor;
an inertial measurement unit configured to determine an orientation of the display unit;
a transmit/receive element configured to receive signals from a set of transmitters in an area wherein the received signals are used to compute a location of the display unit within the area;
a left eye display operably connected to the processor;
a right eye display operably connected to the processor; and
a non-transitory memory configurable to have computer-executable instructions stored thereupon, which when executed by the processor cause the display unit to display a 3D volume stereoscopically to a user wherein a left eye image is displayed on the left eye display and a right eye image is displayed on the right eye display
wherein the location of the display unit within the area changes to a subsequent location closer to the 3D volume;
wherein the transmit/receive element of the display unit receives signals from the set of transmitters in an area;
wherein the processor computes the subsequent location of the display unit within the area;
wherein a zoomed in left eye image is determined by the subsequent location of the display unit, the orientation of the display unit, a left eye viewpoint, a left eye viewing angle, a location of the 3D volume within the area and an orientation of the 3D volume;
wherein a zoomed in right eye image is determined by the subsequent location of the display unit, the orientation of the display unit, a right eye viewpoint, a right eye viewing angle, the location of the 3D volume within the area and the orientation of the 3D volume;
wherein the zoomed in left eye image is displayed on the left eye display; and
wherein the zoomed in right eye image is displayed on the right eye display.

2. The display unit of claim 1 further comprising:
wherein the left eye image is determined by the location of the display unit, the orientation of the display unit, a left eye viewpoint, a left eye viewing angle, a location of the 3D volume and an orientation of the 3D volume; and
wherein the right eye image is determined by the location of the display unit, the orientation of the display unit, a right eye viewpoint, a right eye viewing angle, the location of the 3D volume and the orientation of the 3D volume.

3. The display unit of claim 1 further comprising geo-registering the 3D volume to a first tangible object in the area comprising:
wherein the first tangible object has a transmit/receive element configured to receive signals from the set of transmitters in an area wherein a location of the first tangible object within the area is computed;
wherein the 3D volume is affixed to the first tangible object;
wherein the 3D volume has location coordinates in the area;
wherein a change in the first tangible object's position causes a corresponding change in the 3D volume's position; and
wherein a change in the first tangible object's orientation causes a corresponding change in the 3D volume's orientation.

4. The display unit of claim 1 further comprising:
wherein a location of the 3D volume changes within the area changes to a subsequent location closer to the display unit;
wherein a zoomed in left eye image is determined by the location of the display unit, a left eye viewpoint, a left eye viewing angle, the subsequent location of the 3D volume within the area and an orientation of the 3D volume;
wherein a zoomed in right eye image is determined by the location of the display unit, a right eye viewpoint, a right eye viewing angle, the subsequent location of the 3D volume within the area and the orientation of the 3D volume;
wherein the zoomed in left eye image is displayed on the left eye display; and
wherein the zoomed in right eye image is displayed on the right eye display.

5. The display unit of claim 1 further comprising:
wherein a first tangible object has a transmit/receive element configured to receive signals from the set of transmitters in an area;
wherein the processor computes a location of the first tangible object within the area; and
wherein the movement of the first tangible object on a portion of the 3D volume causes an annotation on the 3D volume.

6. The display unit of claim 1 further comprising a geo-registration point.

7. The display unit of claim 1 further comprising a laser range finder.

8. A display unit comprising:
- a processor;
- an inertial measurement unit configured to determine an orientation of the display unit;
- a transmit/receive element configured to receive signals from a set of transmitters in an area wherein the received signals are used to compute a location of the display unit within the area;
- a left eye display operably connected to the processor;
- a right eye display operably connected to the processor; and
- a non-transitory memory configurable to have computer-executable instructions stored thereupon, which when executed by the processor cause the display unit to display a 3D volume stereoscopically to a user wherein a left eye image is displayed on the left eye display and a right eye image is displayed on the right eye display
- wherein a location of the 3D volume changes within the area changes to a subsequent location closer to the display unit;
- wherein a zoomed in left eye image is determined by the location of the display unit, a left eye viewpoint, a left eye viewing angle, the subsequent location of the 3D volume within the area and an orientation of the 3D volume;
- wherein a zoomed in right eye image is determined by the location of the display unit, a right eye viewpoint, a right eye viewing angle, the subsequent location of the 3D volume within the area and the orientation of the 3D volume;
- wherein the zoomed in left eye image is displayed on the left eye display; and
- wherein the zoomed in right eye image is displayed on the right eye display.

9. The display unit of claim 8 further comprising:
- wherein the left eye image is determined by the location of the display unit, the orientation of the display unit, a left eye viewpoint, a left eye viewing angle, a location of the 3D volume and an orientation of the 3D volume; and
- wherein the right eye image is determined by the location of the display unit, the orientation of the display unit, a right eye viewpoint, a right eye viewing angle, the location of the 3D volume and the orientation of the 3D volume.

10. The display unit of claim 8 further comprising geo-registering the 3D volume to a first tangible object in the area comprising:
- wherein the first tangible object has a transmit/receive element configured to receive signals from the set of transmitters in an area wherein a location of the first tangible object within the area is computed;
- wherein the 3D volume is affixed to the first tangible object;
- wherein the 3D volume has location coordinates in the area;
- wherein a change in the first tangible object's position causes a corresponding change in the 3D volume's position; and
- wherein a change in the first tangible object's orientation causes a corresponding change in the 3D volume's orientation.

11. The display unit of claim 8 further comprising:
- wherein the location of the display unit within the area changes to a subsequent location closer to the 3D volume;
- wherein the transmit/receive element of the display unit receives signals from the set of transmitters in an area;
- wherein the processor computes the subsequent location of the display unit within the area;
- wherein a zoomed in left eye image is determined by the subsequent location of the display unit, the orientation of the display unit, a left eye viewpoint, a left eye viewing angle, a location of the 3D volume within the area and an orientation of the 3D volume;
- wherein a zoomed in right eye image is determined by the subsequent location of the display unit, the orientation of the display unit, a right eye viewpoint, a right eye viewing angle, the location of the 3D volume within the area and the orientation of the 3D volume;
- wherein the zoomed in left eye image is displayed on the left eye display; and
- wherein the zoomed in right eye image is displayed on the right eye display.

12. The display unit of claim 8 further comprising:
- wherein a first tangible object has a transmit/receive element configured to receive signals from the set of transmitters in an area;
- wherein the processor computes a location of the first tangible object within the area; and
- wherein the movement of the first tangible object on a portion of the 3D volume causes an annotation on the 3D volume.

13. The display unit of claim 8 further comprising a geo-registration point.

14. The display unit of claim 8 further comprising a laser range finder.

* * * * *